United States Patent [19]

Meul et al.

[11] Patent Number: 4,997,957

[45] Date of Patent: Mar. 5, 1991

[54] PROCESS FOR THE PRODUCTION OF THIOTETRONIC ACID

[75] Inventors: Thomas Meul; Leander Tenud, both of Visp, Switzerland

[73] Assignee: Lonza, Ltd., Switzerland

[21] Appl. No.: 76,855

[22] Filed: Jul. 23, 1987

Related U.S. Application Data

[63] Continuation of Ser. No. 818,766, Jan. 14, 1986, abandoned.

[30] Foreign Application Priority Data

Jan. 16, 1985 [CH] Switzerland .................. 193/85

[51] Int. Cl.$^5$ .................................. C07D 333/36
[52] U.S. Cl. ........................................ 549/62
[58] Field of Search .......................... 549/62

[56] References Cited

U.S. PATENT DOCUMENTS 2,453,103  2/1944  Turnbull ..................... 260/329

FOREIGN PATENT DOCUMENTS

| 28709 | 1/1980 | European Pat. Off. . |
| 0060808 | 1/1982 | European Pat. Off. . |
| 2214540 | 10/1972 | Fed. Rep. of Germany . |
| 539631 | 7/1973 | Switzerland . |
| 557644 | 1/1975 | Switzerland . |
| 840658 | 7/1960 | United Kingdom . |
| 1266092 | 3/1972 | United Kingdom . |
| 1266093 | 3/1972 | United Kingdom . |
| 1299298 | 12/1972 | United Kingdom . |
| 1299299 | 12/1972 | United Kingdom . |
| 1362143 | 7/1974 | United Kingdom . |
| 1362144 | 7/1974 | United Kingdom . |

OTHER PUBLICATIONS

Chemical Reviews, vol. 86, No. 2 (Apr. 1986), pp. 245 and 246.
D. B. Macierewicz, Rocz. Chem. 47, (1973), p. 1735.
J. Z. Mortensen et al., Tetrahedron 27 (1971), p. 3839.
Wang et al., Tetrahedron Letters, vol. 25, No. 46, pp. 5243–5246 (1984).
E. Benary, Chemische Berichte 46 (1913), pp. 2103 and 2107.
Turnbull, Chem. Abst., vol. 43, (1949), p. 2238.
Chem. Abst., vol. 78, (1973), 29615a.

*Primary Examiner*—Alan Siegel
*Attorney, Agent, or Firm*—Fisher, Christen & Sabol

[57] ABSTRACT

Process for the production of thiotetronic acid wherein 4-chloroacetoacetic acid chloride is reacted with hydrogen sulfide in the presence of an amine.

5 Claims, No Drawings

PROCESS FOR THE PRODUCTION OF THIOTETRONIC ACID

This is a continuation of application Ser. No. 818,766, filed on Jan. 14, 1986, now abandoned.

BACKGROUND OF THE INVENTION

1. Field Of The Invention

The invention relates to a process for the production of thiotetronic acid.

2. Prior Art

It has been reported that thiotetronic acid has been used as an intermediate product for the production of (±) thiolactomycin, an antibiotic having a broad effective spectrum. *Tetrahedron Letters*, Vol. 25, No. 46, pp. 5243 to 5246, (1984) discloses that the dimethyl homologue compound of thiotetronic acid can be used to make (±)-thiolactomycin, an antibiotic having a broad effective spectrum, and the dietyl homologue compound of thiotetronic acid can be used to make thiotetromycin. Accordingly, the *Tetrahedron Letters* letter would cause one skilled in the art to recognize the possible use of thiotetronic acid for the production of a thiolactomycin derivative.

From *E. Benary*, Chemische Berichte 46, 2103 (1913), it is known to produce thiotetronic acid starting out from acetylthioglycoyl chloride as a result of reaction thereof with sodium malonic ester and subsequently ring closure and water treatment. *D.B. Macierewicz*, Rocz. Chem. 47, 1735, (1973), reproduced the reaction of *E. Benary* and obtained at the same time thiotetronic acid at a yield of 30.3 percent, related to the acetylthioglycoyl chloride used. Another possibility for synthesis is set out in *J.Z. Mortensen et al.*, Tetrahedron, 27, 3839, (1971). Starting out from 2,4-dibromothiophene, the thiotetronic acid is obtained in a yield of 46.2 percent by way of three steps as a result of reaction with butyl lithium and t-butylperbenzoate.

In the case of all of the above-identified traditional syntheses, the yields thereof are much too low for a technical or commercial process. Moreover, the processes are hindered by cumbersomeness, expensive educts and by reagents that are difficult to handle.

BROAD DESCRIPTION OF THE INVENTION

An object of the invention is to provide a process for the production of thiotetronic acid which is distinguished by high yields, favorable educts and simple procedure steps. Other objects and advantages of the invention are set out herein or are obvious herefrom to one skilled in the art.

The objects and advantages of the invention are achieved by the process of the invention.

The invention involves preparing thiotetronic acid by treating 4-chloroacetoacetic acid chloride with hydrogen sulfide in the presence of an amine as a base.

DETAILED DESCRIPTION OF THE INVENTION

Effectively one starts with diketene which is converted in a known manner (e.g., published European Patent Application No. 28 709) by chlorination into 4-chloroacetoacetic acid chloride, which can then be adduced in situ for further conversion.

Effectively, operation is conducted in a solvent or solvents. The halogenated hydrocarbons, such as, methylene chloride or chloroform, are advantageous. Methylene chloride is particularly suitable.

As an organic amine, effectively primary, secondary and tertiary amines as well as ammonia and guanidine are used. Preferably, tertiary amines are used; in an especially preferred manner, triethylamine is used.

Hydrogen sulfide is advantageously used in gaseous form.

The educt ratio, in moles, of 4-chloroacetoacetic acid chloride to hydrogen sulfide to amine, is effectively between 1:2:2 and 1:4:3, and preferably between 1 2 5:2 and 1:3.5:2.2.

In order to avoid reaction of the 4-chloroacetoacetic acid chloride with the amines to 4-chloroacetoacetic acid amides or a base catalyzed dimerization into dichlorodehydroacetic acid, the process effectively is conducted in such a way that the acid chloride solution first of all is reacted with hydrogen sulfide and subsequently with the amine. Just as important is the ratio (in moles) of $H_2S$ to amine, for only in the case of an equimolar ratio, better still in the case of excess $H_2S$, will the formation of the above mentioned undesirable by-products be suppressed. The conversion of the acid chloride into the thiotetronic acid is completed immediately after the addition of the amine.

The conversion of the 4-chloroacetoacetic acid chloride is carried out effectively at a temperature of 0° to −40° C., preferably at −10° to −20° C.

The reprocessing of the reaction mixture can be conducted by separation of the solvent as a result of concentration or distillation and by subsequent extraction of the target product from the residue with suitable solvent or solvents. Suitable solvents are ethereal solvents, such as tetrahydrofuran (THF), dioxane or diethyl ether. Diethyl ether is particularly advantageously.

Effectively, the extract solution is treated prior to evaporation for the separation of small quantities of dimeric anhydrothiotetronic acid with an absorption agent, such as, silica gel. After evaporation and drying, the thiotetronic acid can be obtained as a crystalline product.

As used herein, all parts, percentages, ratios and proportions are on a weight basis unless otherwise stated herein or otherwise obvious herefrom to one skilled in the art.

EXAMPLE

From 8.5 g (0.1 mole) of diketene and 7.1 g (0.1 mole) of chlorine, dissolved in 100 ml of methylene chloride, 4-chloroacetoacetic acid chloride was produced according to a known process (i.e., published European Patent Application No. 28,709). This solution was diluted with 500 ml of methylene chloride and was saturated at −15° C. with a gaseous hydrogen sulfide. To this solution, a solution of 20.2 g (0.2 mole) of triethylamine in 180 ml of methylene chloride was added drop by drop at −10° C. within 1.5 hours. (The educt ratio of 4-chloroacetoacetic acid chloride: $H_2S$:triethylamine was 1:3:2.) The temperature of the reaction solution was allowed to rise to room temperature, the solvent was distilled off using a rotation evaporator and the thiotetronic acid was dissolved out of the firm residue in a Soxhlet-extractor with 200 ml of ether. This ether solution was filtered by means of a column filled with silica gel. 7.0 g of orange colored, crystalline product with a content (HPLC) of 88.0 percent was obtained. This corresponded to 6.2 g of 100 percent product (=53.4 percent yield). Melting point: 115° C.

$^1$H-NMR spectrum (300 MHz, DMSO-d$_6$) δ=4.04 (d,2H,J−1, OHz), 5.36 (t,1H), 12.55 (used s,1H).

By way of summary, the invention involves a process for the production of thiotetronic acid by the reaction of 4-chloroacetoacetic acid chloride with hydrogen sulfide in the presence of an amine.

What is claimed is:

1. Process for the production of thiotetronic acid consisting essentially of reacting 4-chloroacetoacetic acid chloride with hydrogen sulfide int he presence of an amine.

2. Process for the production of thiotetronic acid comprising the step consisting of reacting 4-chloroacetoacetic acid chloride with hydrogen sulfide in the presence of an amine.

3. Process for the production of thiotetronic acid comprising the step consisting of reacting 4-chloroacetoacetic acid chloride with hydrogen sulfide in the presence of an amine and in the presence of a halogenated hydrocarbon solvent.

4. Process for the production of thiotetronic acid consisting of reacting 4-chloroacetoacetic acid chloride with hydrogen sulfide in the presence of an amine.

5. Process for the production of thiotetronic acid consisting of reacting 4-chloroacetoacetic acid chloride with hydrogen sulfide in the presence of an amine and in the presence of a halogenated hydrocarbon.

* * * * *